(12) United States Patent
Furnas

(10) Patent No.: US 6,618,495 B1
(45) Date of Patent: Sep. 9, 2003

(54) CONTAINER INSPECTION MACHINE

(75) Inventor: William J. Furnas, Elmira, NY (US)

(73) Assignee: Emhart Glass, S.A., Cham (CH)

( * ) Notice: Subject to any disclaimer, the term of this patent is extended or adjusted under 35 U.S.C. 154(b) by 0 days.

(21) Appl. No.: 09/318,360

(22) Filed: May 25, 1999

Related U.S. Application Data

(63) Continuation-in-part of application No. 09/026,311, filed on Feb. 19, 1998, now Pat. No. 6,031,221.

(51) Int. Cl.$^7$ ................................................. C06K 9/00
(52) U.S. Cl. ..................... 382/142; 382/190; 382/274; 209/526; 250/223 R; 250/559.22
(58) Field of Search ................................ 382/141, 142, 382/149, 190, 191, 274, 273, 220; 250/223 B, 559.08, 559.07, 559.22, 552, 553; 209/526, 524; 356/239.1, 239.4, 239.7, 239.6, 376

(56) References Cited

U.S. PATENT DOCUMENTS

| | | | | |
|---|---|---|---|---|
| 4,270,863 A | * | 6/1981 | Trogdon | 356/71 |
| 4,601,395 A | * | 7/1986 | Juvinall et al. | 209/526 |
| 5,004,909 A | * | 4/1991 | Fukuchi | 356/239.5 |
| 6,031,221 A | * | 2/2000 | Furnas | 209/524 |
| 6,049,379 A | * | 4/2000 | Lucas | 348/127 |
| 6,067,155 A | * | 5/2000 | Ringlien | 250/208.1 |
| 6,134,343 A | * | 10/2000 | Nichani | 382/141 |
| 6,175,107 B1 | * | 1/2001 | Juvinall | 250/223 B |

* cited by examiner

Primary Examiner—Jayanti K. Patel
Assistant Examiner—Sheela Chawan
(74) Attorney, Agent, or Firm—Spencer T. Smith

(57) ABSTRACT

A machine is disclosed for inspecting the wall of a bottle which is delivered by a conveyor sequentially to an inspection station. A light source defined as spatially cyclically continuously varying between the extremes of dark and light.

7 Claims, 2 Drawing Sheets

CONTAINER INSPECTION MACHINE

This application is a continuation-in-part of my application patent application Ser. No. 09/026,311 filed Feb. 19, 1998, now U.S. Pat. No. 6,031,221.

The present invention relates to a machine for inspecting glass or plastic containers such as bottles and more particularly to such a machine which can inspect the sidewall of the container to find defects.

BACKGROUND OF THE INVENTION

The sidewall of a glass container can include various types of defects, including an area of unevenness in glass distribution which will provide a lensing effect when backlit (a refractive defect). Container inspection machines, such as shown in U.S. Pat. No. 5,004,909, inspect the sidewall of a glass bottle by presenting the bottle in front of a light source defined by alternating black and white stripes. Such an inspection machine can find refractive best when they are located at the edge of the stripe. Container inspection machines, such as shown in U.S. Pat. No. 4,601,395, inspect the sidewall of a glass container by presenting the bottle in front of a light source defined by a single bright area that is always in the view of the camera, with transversely spaced outer regions of various intensities and rotating the container.

OBJECT OF THE INVENTION

It is an object of the present invention to provide a container-inspecting machine which will have a higher probability of detecting refractive defects without requiring the container to be rotated.

Other objects and advantages of the present invention will become apparent from the following portion of this specification and from the accompanying drawings which illustrate in accordance with the mandate of the patent statutes a presently preferred embodiment incorporating the principles of the invention.

SUMMARY OF THE INVENTION

The backlight for the inspection is created by using a spatially cyclically continuously varying intensity between the extremes of dark and light intensity. The rate of change is less than that required to be detected as a defect. Refractive defects in the container, through a lens effect, will present to the camera other parts of the light source in a compressed manner. This compression view of the source has a greatly increased rate of change of intensity and thus detected as a defect. The cyclic intensity nature of the illumination permits defect detection throughout the container.

BRIEF DESCRIPTION OF THE PREFERRED EMBODIMENT

Figure 1:
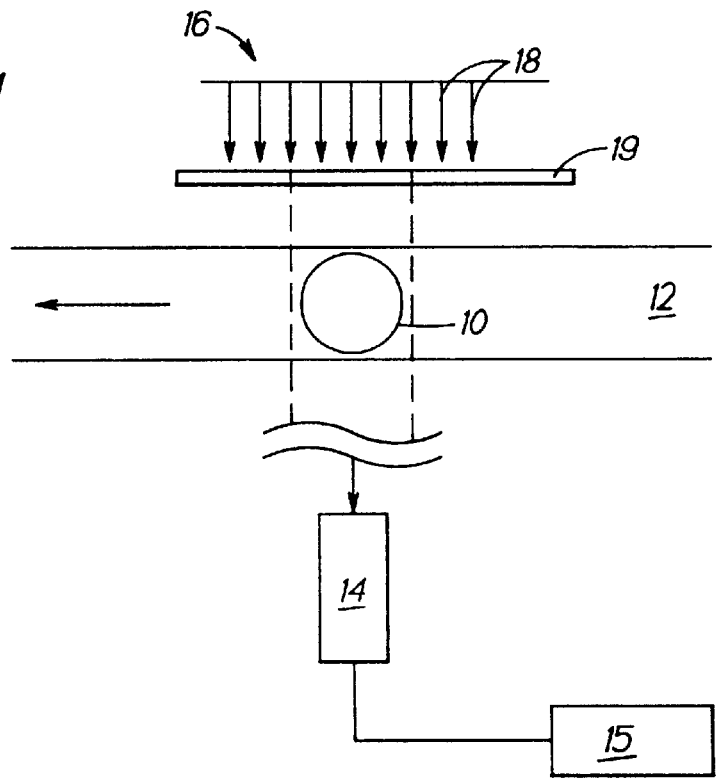
FIG. 1 is a top view of a container inspection machine made in accordance with the teachings of the present invention.

A bottle 10, which can be either glass or plastic is conveyed from right to left along a conveyor 12 for inspection at the illustrated inspection station where the bottle is imaged on the image of a CCD camera 14. The image is evaluated to identify anomalous pixel readings which are indicative of a defect. Associated with the CCD camera is a controlled light source 16 which defines a large area of light. In the preferred embodiment there are a large number of vertical rows of L.E.D.s 18. As can be seen from FIG. 1, the L.E.D.s are focused or aimed so that light will pass through the entire bottle (from top to bottom and from side to side) and be imaged on the camera. These vertical rows also are supported to emit light parallel to each other and the emitted light passes through a diffuser element. Each vertical row of L.E.D.s 18 is turned on and off with a field effect transistor or the like (not shown).

Figure 2:
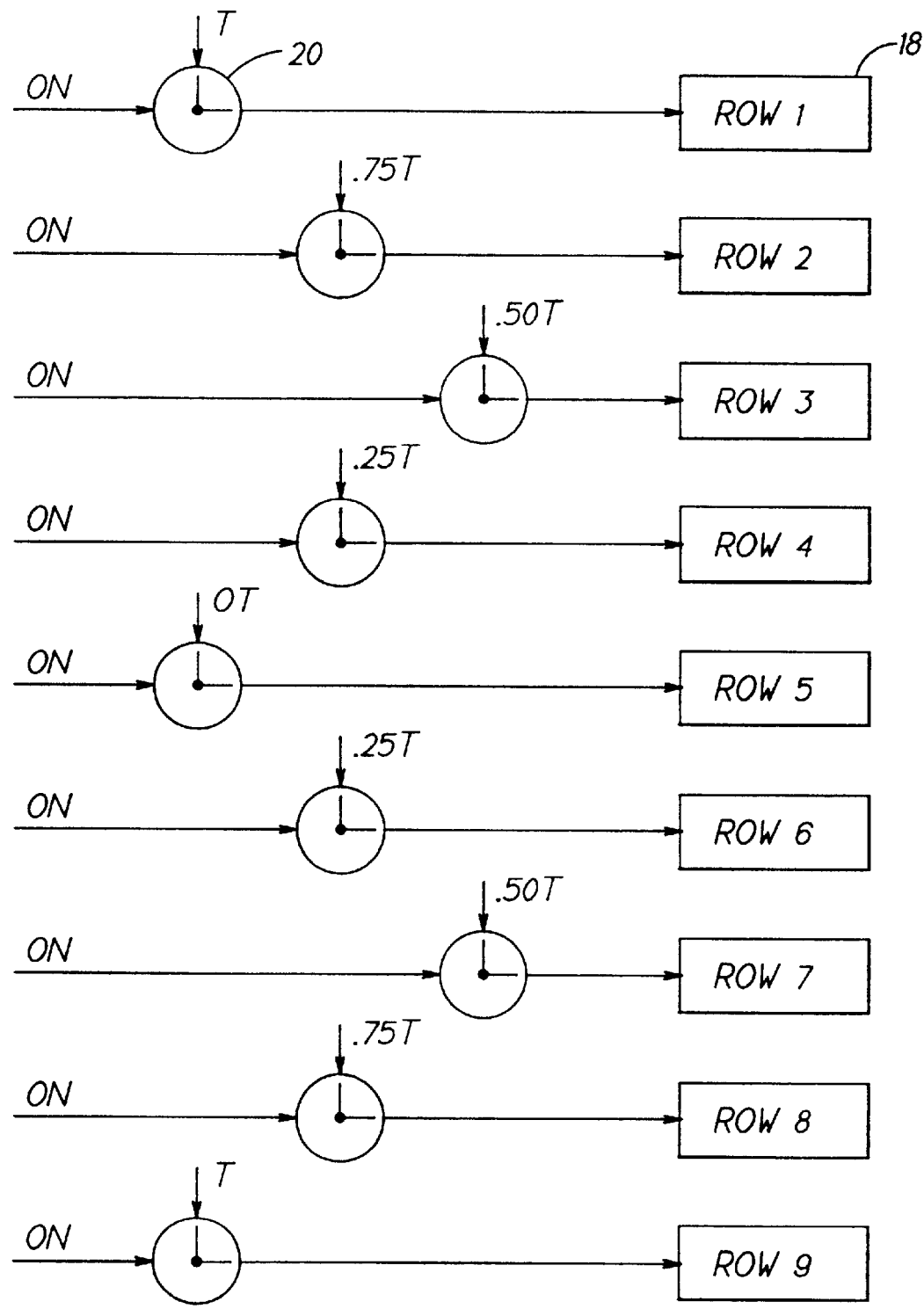
FIG. 2 is schematic representation showing the operation of the light source shown in FIG. 1.

In FIG. 2, an individual timer 20 is connected to each field effect transistor so that when each row can be turned on for a selected time. The timers will time out at selected times (0T,0.25T,0.50T,0.75T,1.0T) of an imaging cycle (here time is equated to the ideal time required for the row of L.E.D. 's to appear illuminated to a selected degree) with light intensity being a function of the time on. For example, 0.50T is the time that a vertical row of lights must be on for the intensity of the row to appear 50%. For discussion purposes the light of a fully on source is referred to as "white", but it should be understood that the light source may be colored and the illuminated light may in fact be invisible (an infrared L.E.D. for example). Actual "on" times may also be varied to compensate for overlapping illumination effects. Due to overlap of light output, actual "on" times, for a particular column, may need to be modified to achieve a best fit to the desired continuously varying intensity cycle. For example, because of light from the 0.25T rows, the black (0T) row may not be as dark as practical and certainly may not reach the ideal of black. To improve the fit to the ideal, the "on" time of the two adjacent %25 bright (0.25T) rows may be set to a reduced on time (0.1T, for example). The same may happen for the full bright (1.0T) columns, which may not get full white because they are getting only partial light from neighboring 0.75T columns, and so the full bright row may need to be set at an increased time on (1.15T, for example). Calculations based upon the actual performance of the illumination method, in this case, L.E.D./diffuser combination, will determine the method of calculating corrections to produce the desired spatially cyclically continuously varying intensity between the extremes of dark and light intensity source.

Figure 3:
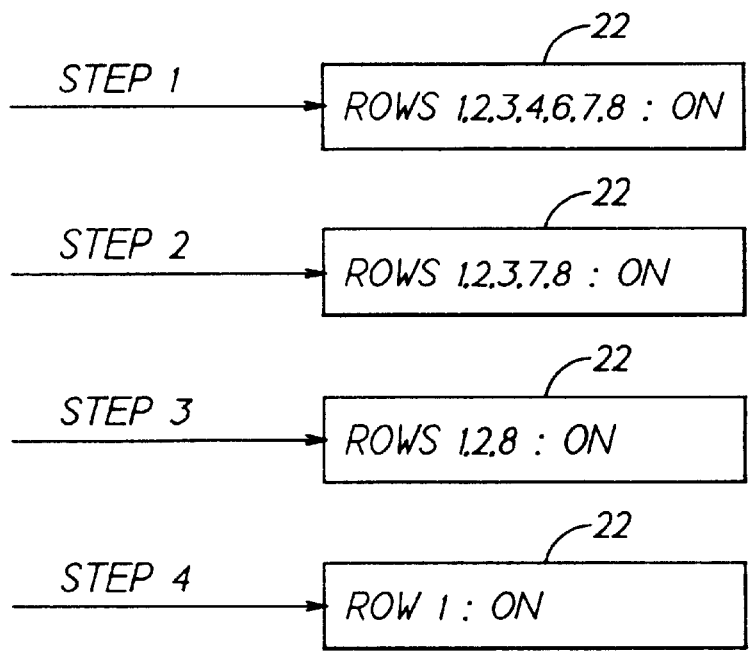
FIG. 3 is a schematic illustration showing the operation of the light source as implemented.

As shown in FIG. 3, a single control operates eight rows and defines bit masks 22 which turn on the desired vertical rows for each of each of the four repeated timed steps (as illustrated each step continues for 0.25T) of an imaging cycle. The image is defined over the period of these four steps. While these illustrations discuss the use of time to set the desired intensity level, current level could alternately be controlled for the same purpose. Other light sources can be used with various light output control over the area methods, such as LCD panel, or printed pattern, in conjunction with a shuttered camera for the same purpose. While there are five intensity levels (0%, 25%, 50%, 75%, and 100%) in the illustrated embodiments, other numbers can be used. With five intensity levels, a light blocking defect can be identified by the CCD camera over 80% of the area of the light source while a refractive defect can be identified over 100% of the area of the light source.

As can be seen from FIG. 3, full control over the individual column intensity goes beyond the fractional linearly calculated percentage previously presented. The pattern presented here could be described as a triangle wave whose peak is a full bright and valley is at black. As can be seen from FIG. 3, full control over the number of columns going from black to bright can be controlled. Changing the number of columns can be done to optimize the cyclic nature of the pattern for a container size or defect size. The spatially varying intensity cycles may be horizontal or vertical or at some other angle. It may also be a combination of angles.

Full control over the relative position of the pattern to the overall backlight (and thus the container to be inspected) can also be controlled. Where the inspection process may use dynamically located zones, the bright portion of the pattern can be optimally placed to aid in the location of the container.

For a one axis cyclic variation, a measure of the light source quality would provide of a nearly flat histogram analysis of the source. A two axis light cyclic light source could also be used to generate such variations with individual LED control, using a transmissive light control scheme such as a light valve, LCD, or printed pattern. A computer 15 analyzes the camera image by comparing neighboring pixels (one or more away) alone or in combination to determine the rate of change in intensity to identify defects where the rate of change exceeds a defined value.

What is claimed is:

1. A machine for inspecting the wall of a bottle comprising
    a conveyor for supporting a bottle at an inspection station,
    the inspection station including
        a CCD camera on one side of the conveyor having a camera image;
        a light source, having an illumination area, on the other side of the conveyor, for imaging the bottle on said CCD camera image;
    means for defining on said illumination area light intensities varying between the extremes of black and a maximum brightness level on said light source illumination area, the intensity of the illumination varying spatially cyclically continuously at a rate of change which is less than that required to be detected as a defect;
    computer means for analyzing said camera image by comparing neighboring pixels (one or more away) alone or in combination to determine the rate of change in intensity to identify defects where the rate of change exceeds a defined value.

2. A machine for inspecting the wall of a bottle according to claim 1, wherein said light source comprises a plurality of L.E.D. rows.

3. A machine for inspecting the wall of a bottle according to claim 2, wherein said plurality of L.E.D. rows define a plurality of row groups each including a row having a maximum intensity at one side, a black row, at least one row intermediate said row having said maximum intensity and said black row having an intensity between black and said maximum intensity, and at least one row on the side of said black row remote from said row having said maximum intensity having an intensity between black and said maximum intensity.

4. A machine for inspecting the profile and wall of a bottle according to claim 3, wherein there are a plurality of vertical L.E.D. rows intermediate the black row and the row having the maximum intensity and the intensity of said plurality of intermediate rows uniformly reduces from the maximum intensity to black.

5. A machine for inspecting the profile and wall of a bottle according to claim 4, wherein there are a plurality of vertical L.E.D. rows on the side of said black row remote from said row having maximum intensity and the intensity of said plurality of said rows on the side of said black row remote from said row having said maximum intensity uniformly increase in intensity proceeding away from the black row.

6. A machine for inspecting the profile and wall of a bottle according to claim 5, wherein each of said vertical L.E.D. row groups has three vertical rows intermediate said black and white rows, with the intensity of the row adjacent the black row having an intensity of about 25% of the intensity of the row having the maximum intensity and the intensity of the row adjacent the row having the maximum intensity having an intensity of about 75% of the maximum intensity and the intensity of t he intermediate of the three vertical rows intermediate the black row and the row having the maximum intensity having an intensity of about 50% of the maximum intensity.

7. A machine for inspecting the profile and wall of a bottle according to claim 6, wherein each of said vertical L.E.D. row groups has three vertical rows on the side of said black row remote from said row having the maximum intensity, with the intensity of the row adjacent the black row having an intensity of about 25% of the maximum intensity and the intensity of the next row having an intensity of about 50% of the maximum intensity and the intensity of the last of the three vertical rows remote from the black row having an intensity of about 75% of the maximum intensity.

* * * * *